United States Patent [19]
Sekula

[11] Patent Number: 5,858,439
[45] Date of Patent: Jan. 12, 1999

[54] REDUCED CALORIE FAT MIMETICS COMPRISING ESTERIFIED PROPOXYLATED MONOGLYCERIDES AND DIGLYCERIDES

[75] Inventor: Bernard C. Sekula, High Bridge, N.J.

[73] Assignee: CPC International Inc., Englewood Cliffs, N.J.

[21] Appl. No.: 435,461

[22] Filed: Jun. 28, 1996

Related U.S. Application Data

[63] Continuation of Ser. No. 601,170, Oct. 19, 1990, abandoned.

[51] Int. Cl.⁶ ........................................ A23L 15/00
[52] U.S. Cl. ..................... 426/531; 426/601; 426/602; 426/603; 554/227
[58] Field of Search ..................... 426/601, 602, 426/603, 531, 606, 607; 554/1, 227

[56] References Cited

U.S. PATENT DOCUMENTS

| | | | |
|---|---|---|---|
| 4,849,242 | 7/1989 | Kershner | 426/601 |
| 4,861,613 | 8/1989 | White et al. | 426/611 |
| 4,963,386 | 10/1990 | Klemann et al. | 426/611 |
| 4,983,329 | 1/1991 | Cooper | 426/611 X |

FOREIGN PATENT DOCUMENTS 0325010  7/1989  European Pat. Off. .

*Primary Examiner*—Leslie Wong
*Attorney, Agent, or Firm*—Norris, McLaughlin & Marcus

[57] ABSTRACT

The present invention relates to esterified propoxylated monoglycerides (EPMG) and diglycerides (EPDG) and reduced calorie food products containing said compounds. Both EPMG and EPDG can be produced in a variety of forms including a liquid form, and can therefore be used for a variety of applications. These compounds are useful as partial or full substitutes for vegetable and other liquid oils, for purposes such as salad oils, cooking oils, anti-spattering or pan-release agents, or as ingredients in products such as mayonnaise, salad dressings, margarines, shortenings and peanut butter. Additionally, these compounds can withstand exposure to heat, and are therefore useful for baking, frying, sauteing and other related applications.

34 Claims, No Drawings

REDUCED CALORIE FAT MIMETICS COMPRISING ESTERIFIED PROPOXYLATED MONOGLYCERIDES AND DIGLYCERIDES

This Application is a Continuation of U.S. Ser. No. 07/601,170 filed Oct. 19, 1990 now abandoned.

FIELD OF THE INVENTION

The present invention relates to reduced calorie fat mimetic materials, and especially to new compounds having desirable combinations of properties and their use in edible compositions.

BACKGROUND OF THE INVENTION

Obesity is one of the most common and prevalent metabolic problems among people today. This condition results from a greater intake of calories than the amount expended. While genetic and behavioral factors play a major role, it is generally agreed that reasonable modifications of the caloric value of foods can be valuable in reaching a desirable equilibrium weight for an individual predisposed to obesity.

Although fats and oils are part of a balanced diet, the average consumer ingests more than is needed for proper nutrition. Fats are consumed directly in meats, spreads, salad oils, and natural produce such as nuts and avocados. Fats and oils are also consumed as a result of their absorption or incorporation in various foods during baking and frying. Because fats and oils play an important role in the organoleptic acceptability of food products, it is very difficult to totally eliminate them. Therefore, for a fat mimetic to be acceptable, it must exhibit good organoleptic qualities, such as mouth feel, have no foreign or unacceptable taste, and have appropriate physical properties for use in food compositions.

DESCRIPTION OF THE RELATED ART

In U.S. Pat. No. 4,861,613 to White et al., non-digestible synthetic fat-type mimetic ingredients comprising esterified epoxide-extended polyols are disclosed and claimed as fat substitutes that exhibit good organoleptic characteristics. They have characteristics similar to vegetable oils and fats, and are substantially resistant to intestinal absorption. The preferred compounds within that group of polyols are acylated propoxylated glycerol mixtures which are resistant to pancreatic lipase in vitro and have been shown in feeding studies to be suitably resistant to overall digestion.

Another known fat substitute is sucrose polyester (SPE) which is disclosed and claimed in U.S. Pat. Nos. 3,251,827 (Schell et al.), 3,600,186 (Mattson et al.) and 3,963,699 (Rizzi et al.) The SPEs are produced by the reaction of a monosaccharide, disaccharide or sugar alcohol having a minimum of four hydroxyl groups with fatty acids having from 8 to 22 carbon atoms. Although the SPEs have the advantage of being suitable for use in both hot and cold applications, an unpleasant side effect to ingestion is anal leakage.

In U.S. Pat. No. 4,849,242 to Kershner, reduced calorie food compositions are claimed wherein at least a portion of the fat content of the food product is replaced with an improved low calorie edible oil substitute that does not cause anal leakage. The substitute taught is an oil-like polymer fatty acid ester which has the property of being substantially hydrolyzed during the process of intestinal digestion into a mixture of fatty acids and a non-caloric water soluble or water-dispersible polymeric alcohol. The fatty acid esters of water soluble polyoxyalkylenes are taught as being particularly useful.

A patent application by Klemann et al. has been filed under the Patent Cooperation Treaty, International Publication No. WO89/01293, which is entitled "Low Calorie Fat Mimetics Comprising Carboxy/Carboxylate Esters". This application discloses and claims fat mimetic compositions which comprise a carbon backbone substituted with carboxylate and/or methyl carboxylate and with carboxy or methylcarboxy functionalities. The preferred carboxy/carboxylate esters are partially but not completely hydrolyzed in the body. These compounds thus achieve reduced caloric value and have fewer of the problems associated with non-metabolizable fat substitutes, such as anal leakage and vitamin stripping. The fat mimetic compounds are useful in all edible compositions.

A new class of reduced calorie oils has now been found wherein the hydroxyl moieties on monoglycerides and diglycerides are propoxylated and subsequently esterified with fatty acids.

SUMMARY OF THE INVENTION

The present invention relates to esterified propoxylated monoglycerides (EPMG) and diglycerides (EPDG) and reduced calorie food products comprising said compounds. EPMG may be prepared by reacting 3-Phenylmethoxy-1,2-propanediol with the desired number of equivalents of propylene oxide in the presence of an effective amount of a basic catalyst such as potassium hydroxide. The 3-phenylmethoxy-1,2-propanediol starting material can be obtained using the procedure described in Sowden, et al., "*J. Am. Chem. Soc.*", 63, 3244 (1941). The propoxylated 3-phenylmethoxy-1,2-propanediol is then reacted with hydrogen in the presence of a transition metal hydrogenolysis catalyst such as palladium. The benzyl ether group is converted to a hydroxyl group in this hydrogenolysis step. Subsequent esterification with fatty acid at an elevated temperature yields the desired product. EPDG may be prepared in an analogous manner using a glycerin-derived starting material having two benzyl ether groups. A more detailed discussion of the processes for producing the presently claimed fat mimetic compounds is set forth in copending patent application Ser. No. 07/600,462, entitled "Process for Producing Esterified Alkoxylated Polyols" by C. F. Cooper, assigned to ARCO Chemical Technology, Inc., and is hereby incorporated by reference.

Both EPMG and EPDG can be produced in a variety of forms including a liquid form, and can therefore be used for a variety of applications. These compounds are useful as partial or full substitutes for vegetable and other liquid oils, for purposes such as salad oils, cooking oils, anti-spattering or pan-release agents, or as ingredients in products such as mayonnaise, salad dressings, margarines, shortenings and peanut butter. Additionally, these compounds can withstand exposure to heat, and are therefore useful for baking, frying, sauteing and other related applications.

A benefit to the use of these compounds is the fact that both EPMG and EPDG are partially hydrolyzed within the body to fatty acids and nonabsorbable digestion residues which are more hydrophilic than the fully esterified substrate. By manipulation of the position and number of oxypropylene groups and types of fatty acids esterified, it is possible to produce fat mimetic compounds having a range of caloric values. Optimally, the fat mimetic compounds should possess minimum caloric value, while avoiding unpleasant side effects, such as vitamin stripping and anal leakage which are associated with non-hydrolyzable fat substitutes and mimetics.

DETAILED DESCRIPTION OF THE INVENTION

The present invention relates to fat mimetics comprising EPMGs and EPDGs and their incorporation in various reduced calorie food products. These fat mimetics have the formula:

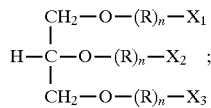

where R is oxypropylene

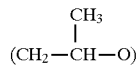

and subscript n is zero (0) or an independently selected integer such that the sum of the ns is from 1 to 14 and one or two ns are zero, and $X_1$, $X_2$ and $X_3$ are the same or different fatty acid residues comprising from 2 to 24 carbon atoms.

EPMGs and EPDGs are formed by the propoxylation of the hydroxyl residues of monoglycerides and diglycerides followed by esterification with fatty acids. EPMGs and EPDGs are characterized by the incomplete propoxylation of the glycerol backbone, in contrast to the total propoxylation of glycerol as previously claimed in U.S. Pat. No. 4,861,613. Specifically, by not fully propoxylating the glycerol backbone glyceride esters, which are sensitive to lipase activity, are available. A fat mimetic comprising EPMG may exhibit the following formula:

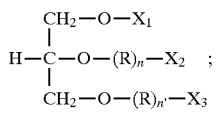

In this formula R is oxypropylene

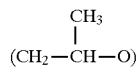

present in an amount such that the sum of the integers n and n' is in the range of from 1 to 14 preferrably in the range of from 1 to 8, wherein n and n' may be the same or different integers and wherein $X_1$, $X_2$ and $X3$ are the same or different fatty acid residues comprising from 2 to 24 carbon atoms.

An alternate embodiment of a fat mimetic comprising EPMG has the formula:

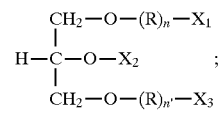

wherein R, $X_1$, $X_2$, $X_3$, n and n' are defined as above. Since lipolytic enzymes generally exhibit 1, 3-positional specificity, this alternate embodiment would be expected to provide fewer calories upon ingestion.

By not fully propoxylating the glycerol backbone of the EPMG compound, the lipase enzymes are able to hydrolyze the non-propoxylated branch of the compound, resulting in partial absorption in vivo. Since the fat mimetic is partially digested in the body, the undesirable side effects of vitamin stripping and anal leakage do not occur.

An alternate to EPMG, wherein one glycerol ester is not propoxylated, is EPDG, wherein two glycerol esters are without oxypropylene groups. The fat mimetic comprising EPDG may have the formula:

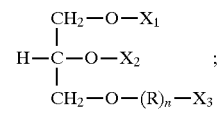

In this formula R is oxypropylene

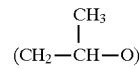

present in an amount such that the value of subscript n is from 1 to 14 preferably from 1 to 8 and wherein $X_1$, $X_2$ and $X_3$ are the same or different fatty acids residues comprising from 2 to 24 carbon atoms.

A total inversion of this formula, placing the oxypropylene group or groups in the number one position, is also an acceptable and functionally equivalent form of this compound and is shown below.

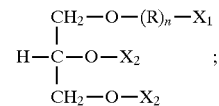

As an alternate embodiment of the fat mimetic comprising EPDG, the oxypropylene group or groups can be moved from the one or three position to the two position in the compound resulting in a fat mimetic having the formula:

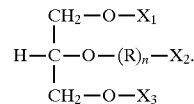

As previously stated, both EPMG and EPDG can be partially hydrolyzed due to the existence of the non-propoxylated glycerol esters. Relatively speaking, the greatest degree of hydrolysis will be exhibited with the EPDG compound wherein the oxypropylene group or groups are attached to the two position of the glycerol backbone. The EPDG compound with the oxypropylene group or groups at either the one or three position will have a degree of hydrolysis approximately equal to that form of the EPMG compound wherein the non-propoxylated glycerol ester is in the number one position of the backbone. The compound exhibiting the lowest level of hydrolysis will be the EPMG compound wherein the oxypropylene groups are present in the one and three position surrounding the non-propoxylated glycerol ester at the two position.

The caloric value of the food products incorporating the reduced calorie fat mimetics will be directly related to the degree of hydrolysis of the compounds. It has been shown that the fat mimetic compounds are hydrolyzed by pancreatic lipases in vitro. The percent of hydrolysis depends upon the compounds as discussed above, and takes into account the molecular weight of the compound. For example, EPMG-08 (where 08 is the average propoxylation number) hydrolyzes at a rate of approximately 1% as compared to the rate of hydrolysis of olive oil. EPDG-08 hydrolyzes at a rate of approximately 11% as compared to olive oil and EPDG-04 at a rate of approximately 15% as compared to olive oil. It is anticipated that over longer periods of time, i.e. more comparable to times that food is retained in the body such as 5 to 6 hours, the fat mimetic compounds will be hydrolyzed to the extent of approximately one-third that of olive oil.

The number of oxypropylene groups can vary in each compound from a level of from 1 to 14, with the preferred range being from 1 to 8. The propoxylation number of the compound, including the range set forth herein, refers to the average number of oxypropylene groups in the final product, and not necessarily a fixed number on a molecular basis. Therefore, the range being claimed is the range for the average propoxylation number of the final compound.

The fatty acids which can be used comprise a variety of fatty acids with from 2 to 24 carbon atoms, preferably from 10 to 22 carbon atoms. Examples of such fatty acids are acetic, butyric, caprylic, capric, lauric, myristic, myristoleic, palmitic, palmitoleic, heptadecanoic, stearic, oleic, ricinoleic, linoleic, linolenic, arachidic, behenic, and erucic.

The fatty acids can be derived from suitable naturally occuring or synthetic fatty acids and can be saturated or unsaturated, including positional and geometric isomers, depending on the desired physical properties of the resulting fat mimetic. Naturally occurring fats and oils can serve as the source for the fatty acid component in the compound. For example, rapeseed oil provides a good source for $C_{22}$ fatty acid. $C_{16}$–$C_{18}$ fatty acids can be provided by tallow, soybean oil or cottonseed oil. Shorter chain fatty acids can be provided by coconut, palm kernel or babassu oils. Corn oil, lard, olive oil, palm oil, peanut oil, safflower seed oil, sesame seed oil, sunflower seed oil and menhaden fish oil are examples of other natural oils which can serve as the source of the fatty acid component. Among the fatty acids, those that are preferred are selected from the group consisting of acetic, butyric, palmitic, stearic, oleic, linoleic and behenic. The choice of the fatty acids to be used is directly related to the caloric value of the food compound in which they are to be incorporated.

Manipulation of the fatty acids within the structure, in addition to altering the structure itself, may result in a change in the caloric value of the food product. Additionally, manipulation of the fatty acids affects the physical properties of the product, and may result in solid or liquid fat mimetics. The optimal configuration of the fat mimetic would comprise short chain fatty acids esterified to the hydroxyl residues of glycerol and long chain fatty acids esterified to the terminal oxypropylene groups. This combination would result in a minimum caloric value in the food product.

The resulting fat mimetic products can be used for a variety of purposes including substitutes for liquid oils, such as in salad dressings, as the fat component in a baked product such as a cake, or as a frying or sauteing agent. Additionally, the fat mimetic products can be used as anti-spattering or pan-release agents. Depending upon the food product, and upon the desired final caloric value, fat mimetics comprising EPMGs and/or EPDGs can be substituted at levels of up to 100% of the fat component in the food product. Fat mimetics comprising EPMGs and EPDGs can be used alone as substitutes for fats, or can be used in combination as substitutes in any of the above defined applications.

The following examples further illustrate various features of the invention, but are not intended in any way to limit the scope of the invention which is described in the appended claims.

EXAMPLE 1

A vinaigrette dressing was prepared using the following ingredients:

1.0 grams table salt
0.15 grams white ground pepper
2.0 grams dijon mustard
20.0 grams wine vinegar
40 grams oil or fat mimetic All the ingredients were weighed into an eight ounce jar and shaken to blend. Two tablespoons of the dressing were spooned over 60 grams of lettuce and tossed. The remaining dressing was left in the jar to evaluate the separation.

The vinaigrette dressing was prepared using both soybean oil (as a CONTROL) and EPMG-08 and the results are summarized below:

|  | CONTROL | EPMG-08 |
| --- | --- | --- |
| Aroma | Typical | Typical |
| Appearance | Separate phases/ milky layer | Remained one phase/ Pink/red color |
| Texture | Typical; oily Did not cling well to lettuce. | More body than control. Clung well to lettuce. |

EXAMPLE 2

Pancake batter was prepared using the following ingredients:

½ cup AUNT JEMIMA ORIGINAL PANCAKE MIX
½ cup whole milk
1 egg
1 tablespoon oil or fat mimetic All the ingredients were whisked together and placed in an aluminum fry pan. The fry pan contained 22 grams of the oil or fat mimetic as the frying medium, and was heated on a gas burner at high for one minute prior to the batter being introduced therein. Upon bubbling, the pancakes were turned and cooked for an additional thirty seconds on the second side. They were thereafter removed from the pan. The following was observed:

|  | Run 1 | | Run 2 | |
|---|---|---|---|---|
|  | CONTROL 1 | EPMG-08 | CONTROL 2 | EPDG-08 |
| Preparation: | | | | |
| Heating | Typical | | Typical | Faster than CONTROL |
| Cooking | Typical | Quicker than CONTROL | Typical | Faster than CONTROL |
| Coating | Typical | Coated pan better than CONTROL | Typical | Coated pan better than CONTROL |
| Aroma | Typical | Typical | Typical | Typical |
| Appearance | Greasy; not evenly browned | Not greasy; evenly browned | Slightly greasy; not evenly browned | Not greasy; evenly browned |
| Texture | Not so fluffy | Fluffy | Acceptable | Fluffier than control |

CONTROL 1 was soybean oil, both in the pan and in the mix.
CONTROL 2 was corn oil, both in the pan and in the mix.

EXAMPLE 3

A vegetable saute was prepared using 125 grams of green bell pepper slices, 100 grams of mushroom slices and 100 grams of onion slices. 22 grams of an oil or fat mimetic were placed in an aluminum fry pan and heated on a gas burner on High for one minute. The vegetables were added and stirred, and cooked for eight minutes on high. Thereafter, they were removed from the pan. The results are as outlined below:

|  | Run 1 | | Run 2 | |
|---|---|---|---|---|
|  | CONTROL 1 | EPMG-08 | CONTROL 2 | EPDG-08 |
| Preparation: | | | | |
| Heating | Typical | Quicker than control | Typical | Quicker than control |
| Cooking | Typical | Quicker than CONTROL | Typical | Quicker than CONTROL |
| Coating | Not so well | Coated vegetables well | Typical | Coated vegetables well |
| Aroma | Typical | Typical | Typical | Typical |
| Appearance | Typical moderate browning | Glistening/ slight browning | Typical | Glistening/ more attractive |
| Flavor | — | — | Typical | Typical |
| Texture | Slightly steamed | Crisp | Slightly steamed | Crisp |

CONTROL 1 was soybean oil.
CONTROL 2 was corn oil.

EXAMPLE 4

A reduced calorie mayonnaise product was prepared by replacing 100% of the oil component with EPMG-08 as shown in the following formula:

| Inqredient | Percent by weight |
|---|---|
| EPMG-08 | 77.00 |
| Water | 8.50 |
| Vinegar | 2.50 |
| Egg and Flavorants | 12.00 |
|  | 100.00 |

The resulting mayonnaise product had an acceptable texture and flavor.

EXAMPLE 5

A reduced calorie salad dressing product was prepared by replaing 100% of the oil component with EPDG-08 as shown in the following formula:

| Inqredient | Percent by weight |
|---|---|
| EPDG-08 | 32.50 |
| Starch Paste | 56.00 |
| vinegar | |
| sugar | |
| starch | |
| gum | |
| water | |
| Egg Yolk and Flavorants | 11.50 |
|  | 100.00 |

The resulting salad dressing product exhibited acceptable texture and flavor.

What is claimed is:

1. A fat mimetic having the formula:

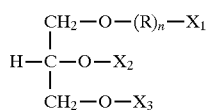

wherein R is oxypropylene

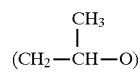

present in an amount such that n is from 1 to 14 and $X_1$, $X_2$ and $X_3$ are the same or different fatty acid residues comprising from 2 to 24 carbon atoms, and wherein said fat mimetic has a glycerol backbone which is not fully propoxylated.

2. The fat mimetic of claim 1 wherein n is from 1 to 8.

3. A reduced calorie food product having an edible oil component wherein from about 5 to about 100% of the edible oil in said food product is comprised of the fat mimetic of claim 1.

4. The reduced calorie food product of claim 3 wherein the food product is partly digestible.

5. The reduced calorie food product of claim 3 comprising a liquid oil.

6. The reduced calorie food product of claim 3 comprising a spoonable or pourable salad dressing product.

7. The reduced calorie food product of claim 3 comprising a mayonnaise product.

8. The reduced calorie food product of claim 3 comprising a margarine.

9. The reduced calorie food product of claim 3 comprising a peanut butter product.

10. The reduced calorie food product of claim 3 comprising a shortening.

11. A fat mimetic having the formula:

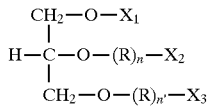

wherein R is oxypropylene

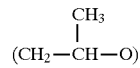

present in an amount such that the sum of n and n' is from 1 to 14, wherein n and n' are the same or different integers and $X_1$, $X_2$ and $X_3$ are the same or different fatty acid residues comprising from 2 to 24 carbon atoms, and wherein said fat mimetic has a glycerol backbone which is not fully propoxylated.

12. The fat mimetic of claim 11 wherein the sum of n and n' is from 1 to 8.

13. A reduced calorie food product having an edible oil component wherein from about 5 to about 100% percent of the edible oil in said food product is comprised of the fat mimetic of claim 11.

14. The reduced calorie food product of claim 13 wherein the food product is partly digestible.

15. The reduced calorie food product of claim 13 comprising a liquid oil.

16. The reduced calorie food product of claim 13 comprising a spoonable or pourable salad dressing product.

17. The reduced calorie food product of claim 13 comprising a mayonnaise product.

18. The reduced calorie food product of claim 13 comprising a margarine.

19. The reduced calorie food product of claim 13 comprising a peanut butter product.

20. The reduced calorie food product of claim 13 comprising a shortening.

21. A fat mimetic having the formula:

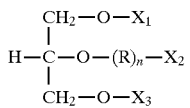

wherein R is oxypropylene

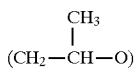

present in an amount such that n is from 1 to 14 and $X_1$, $X_2$ and $X_3$ are the same or different fatty acid residues comprising from 2 to 24 carbon atoms, and wherein said fat mimetic has a glycerol backbone which is not fully propoxylated.

22. The fat mimetic of claim 21 wherein n is from 1 to 8.

23. A reduced calorie food product having an edible oil component wherein from about 5 to about 100% of the edible oil in said food product is comprised of the fat mimetic of claim 21.

24. The reduced calorie food product of claim 23 wherein the food product is partly digestible.

25. The reduced calorie food product of claim 23 comprising a liquid oil.

26. The reduced calorie food product of claim 23 comprising a spoonable or pourable salad dressing product.

27. The reduced calorie food product of claim 23 comprising a mayonnaise product.

28. The reduced calorie food product of claim 23 comprising a margarine.

29. The reduced calorie food product of claim 23 comprising a peanut butter product.

30. The reduced calorie food product of claim 23 comprising a shortening.

31. A fatty product effective for frying foods comprising a compound as defined in any one of claims 1, 11, or 21.

32. An edible oil useful in producing baked products comprising a compound as defined in any one of claims 1, 11 or 21.

33. A reduced calorie food product having an edible oil component wherein from about 5 to about 100% of the edible oil component is comprised of any combination of the fat mimetics set forth in any one of claims 1, 11, or 21.

34. An edible oil comprising a compound as defined in any one of claims 1, 11, or 21, wherein said edible oil is useful in producing baked food products.

* * * * *